US008894815B2

(12) United States Patent
Farrar et al.

(10) Patent No.: US 8,894,815 B2
(45) Date of Patent: Nov. 25, 2014

(54) STORAGE STABLE SOLUTIONS OF OPTICAL BRIGHTENERS

(75) Inventors: John Martin Farrar, Leeds (GB); Andrew Clive Jackson, Münchenstein (CH); Margaret Mahon, West Yorkshire (GB); Martin Oberholzer, Witterswil (CH)

(73) Assignee: Clariant Finance (BVI) Limited, Tortola (VG)

( * ) Notice: Subject to any disclaimer, the term of this patent is extended or adjusted under 35 U.S.C. 154(b) by 487 days.

(21) Appl. No.: 12/746,024

(22) PCT Filed: Dec. 9, 2008

(86) PCT No.: PCT/EP2008/067070
§ 371 (c)(1),
(2), (4) Date: Aug. 12, 2010

(87) PCT Pub. No.: WO2009/074548
PCT Pub. Date: Jun. 18, 2009

(65) Prior Publication Data
US 2010/0294447 A1    Nov. 25, 2010

(30) Foreign Application Priority Data
Dec. 12, 2007  (EP) ...................................... 07123044

(51) Int. Cl.
  D21H 21/30    (2006.01)
  D21H 17/07    (2006.01)
  D21H 17/09    (2006.01)
  D21H 23/04    (2006.01)
  D21H 23/22    (2006.01)
  C09K 11/00    (2006.01)
  C09K 11/06    (2006.01)
  C07D 251/00   (2006.01)
  C07D 251/38   (2006.01)
  C07D 251/40   (2006.01)

(52) U.S. Cl.
  USPC ........... 162/162; 162/184; 162/185; 162/158; 8/648; 252/301.16; 252/301.21; 252/301.23; 427/157; 427/158; 544/193.2; 544/194

(58) Field of Classification Search
  USPC ............... 162/72, 158, 162, 184, 185; 8/648; 427/157, 158; 442/130; 252/301.16, 252/301.21, 301.23; 544/193.2, 194
  See application file for complete search history.

(56) References Cited

U.S. PATENT DOCUMENTS

| 3,012,971 A | 12/1961 | Gessner |
| 4,339,238 A | 7/1982 | Fringeli et al. |
| 4,562,002 A * | 12/1985 | Neiditch et al. ............... 510/516 |
| 5,904,739 A | 5/1999 | Martini et al. |
| 6,890,454 B2 * | 5/2005 | Farrar et al. .............. 252/301.21 |
| 7,060,201 B2 * | 6/2006 | Farrar ........................ 252/301.23 |
| 7,270,771 B2 * | 9/2007 | Cuesta et al. ............. 252/301.23 |
| 7,300,474 B2 | 11/2007 | Zirkenbach et al. |
| 8,221,588 B2 | 7/2012 | Farrar et al. |
| 2003/0089888 A1 | 5/2003 | Bacher et al. |
| 2004/0074021 A1 * | 4/2004 | Farrar et al. ........................ 8/648 |
| 2006/0211593 A1 * | 9/2006 | Smith et al. ................... 510/424 |
| 2006/0260509 A1 * | 11/2006 | Evers ............................ 106/234 |
| 2010/0159763 A1 * | 6/2010 | Farrar et al. .................. 442/130 |

FOREIGN PATENT DOCUMENTS

| EP | 0884312 | 12/1998 |
| EP | 1300514 | 4/2003 |
| EP | 1752453 | 2/2007 |
| EP | 1 912 955 B1 | 4/2008 |
| EP | 1 352 046 B1 | 3/2011 |
| GB | 1243276 A | 8/1971 |
| GB | 1369202 | 10/1974 |
| JP | 62-273266 | 11/1987 |
| JP | H-09118835 A | 5/1997 |
| JP | 2005-526872 A | 9/2005 |
| WO | WO 2005/028749 | 3/2005 |
| WO | WO 2007/017336 | 2/2007 |
| WO | WO 2007/017336 A1 * | 2/2007 |

OTHER PUBLICATIONS

PCT International Search Report for PCT/EP2008/067070, mailed Aug. 10, 2009.
English Abstract for JP 62-273266, Nov. 27, 1987.

* cited by examiner

Primary Examiner — Dennis Cordray
(74) Attorney, Agent, or Firm — Miles & Stockbridge, P.C.

(57) ABSTRACT

The instant invention relates to storage stable solutions of optical brighteners based on certain salt forms of anilino-substituted bistriazinyl derivatives of 4,4'-diaminostilbene-2,2'-disulphonic acid and of organic acids which do not need extra solubilizing additives.

16 Claims, No Drawings

STORAGE STABLE SOLUTIONS OF OPTICAL BRIGHTENERS

The instant invention relates to storage stable solutions of optical brighteners based on derivatives of diaminostilbene which do not need extra solubilising additives.

It is well known that the whiteness and thereby the attractiveness of paper, board, textile and non-woven products can be improved by the addition of optical brightening agents (OBAs). The most important optical brighteners in the paper and board industry are anilino-substituted bistriazinyl derivatives of 4,4'-diaminostilbene-2,2'-disulphonic acid. The anilino-substituent may contain additional sulphonic acid groups, which provide a greater water-solubility. The optical brightener of formula (A, M=Na) in which the anilino-substituent contain no sulphonic acid groups has a particularly high affinity for cellulose fibres and is especially suitable for use at the wet-end of the paper making process.

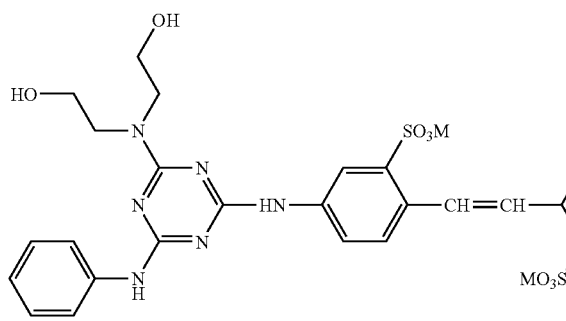
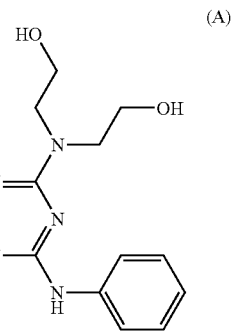

(A)

For ease of handling and metering, the paper and board industry demands that optical brighteners be supplied in a liquid form, preferably in the form of a concentrated aqueous solution. Furthermore, the liquid form has to be stable to prolonged storage over a wide temperature range, typically 4 to 50° C. In the past, solubilising auxiliaries such as urea or ethylene glycol have been added in amounts of up to 30% by weight in order to provide aqueous solutions of (A) which are stable to storage. These solubilising agents have no affinity for cellulose, however, and contaminate the effluent from the paper mill.

EP-A-884 312 provides a partial solution to this problem by disclosing that certain hydrates of (A, including M=Na) may be used to produce stable liquid suspensions or slurries containing low amounts of formulation auxiliaries.

EP-A-1 300 514 offers another partial solution by disclosing concentrated aqueous brightener preparations of (A, including M=Na) which remain stable at elevated temperatures of between 40 and 98° C.

WO 2007/017336 A1 discloses storage stable solutions of optical brighteners based on certain salt forms of anilino-substituted bistriazinyl derivatives of 4,4'-diaminostilbene-2,2'-disulphonic acid which do not need extra solubilising additives.

WO 2005/028749 A1 discloses optical brightener compositions comprising an alkanolamine and an optical brightener of formula A (M=H). Preferred alkanolamines are 2-amino-2-methyl-1-propanol, 1-amino-2-propanol or a mixture of 2-amino-2-methyl-1-propanol and 2-(N-methylamino)-2-methyl-1-propanol.

Japanese Kokai 62-273266 claims optical brightener compositions comprising quaternary ammonium salts of anionic bis(triazinylamino) stilbene derivatives. The preferred quaternary ammonium ion is a trimethyl-β-hydroxyethylammonium ion.

The demand remains for stable, concentrated aqueous solutions of disulphonated optical brighteners, which are free from solubilising auxiliaries.

It has now surprisingly been found that a specific salt form of (A) in combination with small amounts of organic acids enables stable concentrated solutions to be formed, without the addition of solubilising auxiliaries.

The present invention therefore provides an aqueous solution containing 10 to 40% by weight of a compound of formula (1)

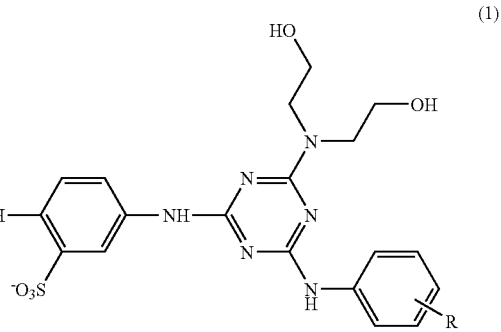

(1)

$[M^+]_n[(CH_3)_2NH^+CH_2CH_2OH]_{2-n}$ in which
R is hydrogen or a methyl radical,
$M^+$ is $Li^+$, $Na^+$, or $K^+$, and
n is less than or equal to 1.5, and
of 0.05 to 5% by weight of an organic acid selected from citric acid, glycolic acid, acetic acid or formic acid.

As demonstrated by example 5 the use of organic acids instead of hydrochloric acid (as used in WO 2007/017336 A1 with a similar optical brightener) leads to a much better storage stability.

Preferred are aqueous solutions containing 15 to 35% by weight of a compound of formula (1) in which
R is hydrogen or a methyl radical,
$M^4$ is $Na^+$, and
n is less than or equal to 1.5, and
of 0.1 to 2% by weight of citric acid.

More preferred are aqueous solutions in which
R is hydrogen,
$M^+$ is $Na^+$, and
n is less than or equal to 1.5.

Especially preferred are aqueous solutions in which
R is hydrogen,
$M^+$ is $Na^+$, and
n is less than or equal to 1.2.

The present invention also provides a process for the production of the above aqueous solutions, the process being characterised in that a compound of formula (2)

The instant aqueous solutions may optionally contain one or more carriers, antifreezes, defoamers, solubilizing aids, preservatives, complexing agents etc., as well as organic by-products formed during the preparation of the optical brightener.

Carriers are known to give improved whitening characteristics to pigmented coating brightener compositions and may be, e.g., polyethylene glycols, polyvinyl alcohols or carboxymethylcelluloses.

Antifreezes may be, e.g., urea, diethylene glycol or triethylene glycol.

Solubilizing aids may be, e.g., urea, triethanolamine, triisopropanolamine or 2-dimethylaminoethanol.

The instant aqueous solutions are suitable for use as optical brighteners for the whitening of textiles, paper, board and non-wovens. They are particularly useful for the whitening of paper and board, and are suitable for application either to an aqueous suspension of pulp, or to the surface of paper, especially in a pigmented coating composition. They are characterized by high storage stability, yield and ease of application. They are also highly compatible with other additives conventionally employed in the production of cellulosic articles, especially paper and board.

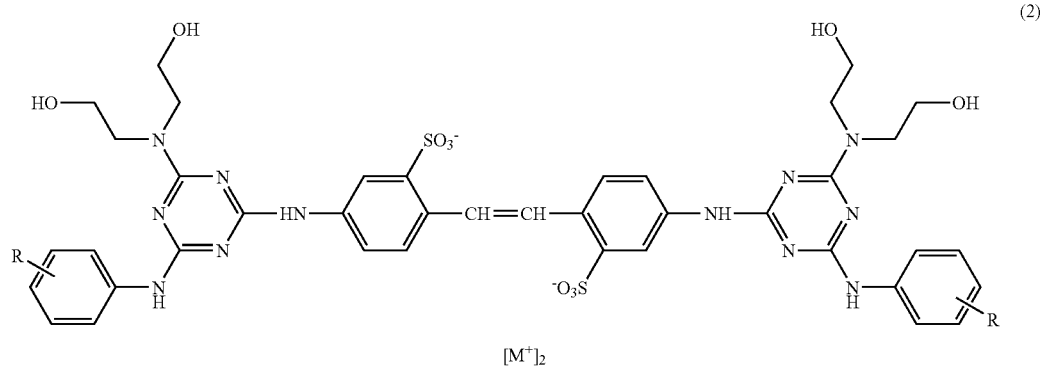

(2)

wherein R is hydrogen or a methyl radical, in the form of an aqueous solution is converted to a mixed salt form (1) in which at least 25% of the $M^+$ ions associated with the sulphonate groups have been replaced by $(CH_3)_2NH^+CH_2CH_2OH$ ions, by treatment with 2-dimethylaminoethanol and an organic acid (for example acetic, formic, tartaric or citric acid).

EXAMPLES

The following examples shall demonstrate the instant invention in more details. If not indicated otherwise, "parts" means "parts by weight" and "%" means "% by weight".

Example 1

220 parts of diethanolamine are added at 60° C. to a stirred suspension of 824 parts of a compound of formula (3)

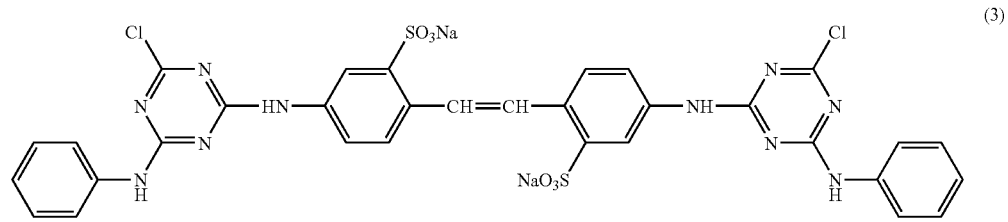

(3)

in 7750 parts water. The mixture is heated to reflux and maintained there for 4 hours while controlling the pH to 8.5-9.0 by the addition of sodium hydroxide in the form of a 30% aqueous solution. 44 parts of sodium chloride are added, and the mixture is stirred at reflux for a further 10 minutes. The mixture is then cooled to 90° C. before stirring is stopped. After standing for 10 minutes, the lower phase of oil (1990 parts) containing a compound of formula (A, M=Na) is separated from the salt-containing aqueous phase and added at 80° C. with stirring to 1570 parts cold water. The solution so-fanned is then treated at 50° C. with a solution of 300 parts 2-dimethylaminoethanol in 350 parts cold water and 212 parts citric acid. The mixture is stirred at 50° C. for 10 minutes, then kept at 50° C. After standing for 1 hour, the lower phase of oil is separated, and diluted with water to give 4400 parts of an aqueous solution containing 22.0% of a compound of formula (4) and 0.5% of citric acid.

Example 4

Example 1 is repeated using 252 parts of glycolic acid in place of 212 parts of citric acid. The aqueous solution of (4) and 0.6% glycolic acid so-formed is stable to storage at 4° C. for at least two weeks either in the absence or presence of crystal seeds.

Example 5

Comparative Example to Show Advantage Over the Use of the Hydrochloride Salt of 2-Dimethylaminoethanol Example 1 is repeated using 326 parts of 37% hydrochloric acid in place of 212 parts of citric acid. The aqueous solution

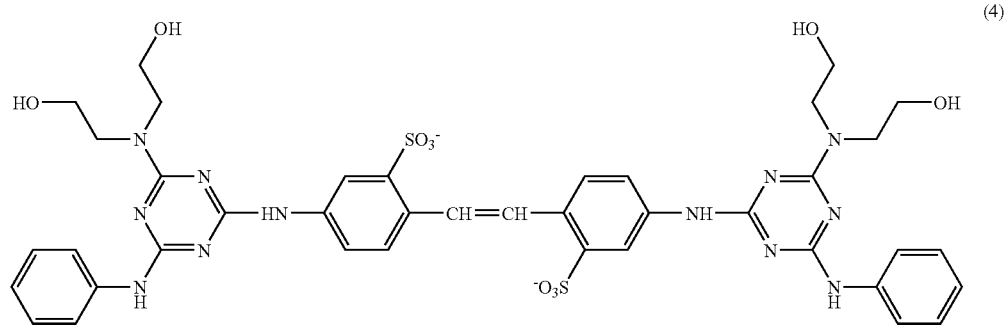

The aqueous solution so-formed is stable to storage at 4° C. for at least two weeks either in the absence or presence of crystal seeds.

Example 2

Example 1 is repeated using 152 parts of formic acid in place of 212 parts of citric acid. The aqueous solution of (4) and 0.4% formic acid so-formed is stable to storage at 4° C. for at least two weeks either in the absence or presence of crystal seeds.

Example 3

Example 1 is repeated using 199 parts of acetic acid in place of 212 parts of citric acid. The aqueous solution of (4) and 0.5% acetic acid and so-formed is stable to storage at 4° C. for at least two weeks either in the absence or presence of crystal seeds.

of (4) so-formed precipitates within 4 days on storage at 4° C. in the presence of crystal seeds.

Example 6

Comparative Example to Show Advantage Over the $(CH_3)_3N^+CH_2CH_2OH$ Counter-Ion (Claimed in Japanese Kokai 62-273266)

Example 1 is followed up to the point where the oil (1990 parts) is first separated from the salt-containing aqueous phase. The oil is then poured into a stirred solution of 309 parts choline chloride in 2700 parts water. After standing for 1 hour, the lower phase of oil is separated, and diluted with water to give 4400 parts of an aqueous solution containing 22.4% of a compound of formula (5).

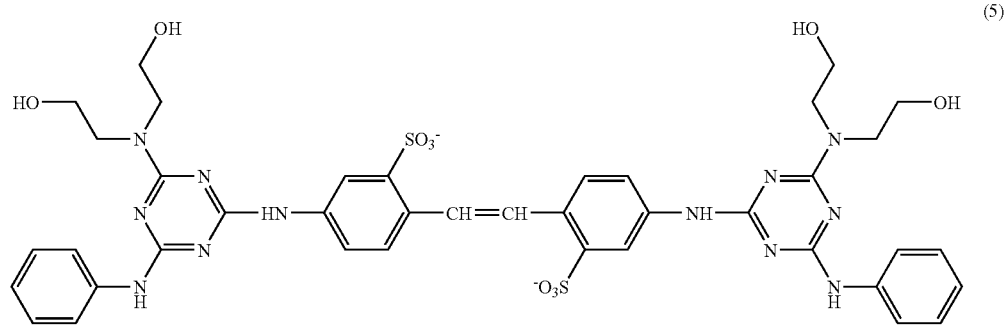

(5)

$[Na^+]_{0.7}[(CH_3)_2N^+CH_2CH_2OH]_{1.3}$

The aqueous solution so-formed precipitates within 4 days on storage at 4° C. in the presence of crystal seeds.

Example 7

Comparative Example to Show Advantage Over the $(CH_3)_2C(NH_3^+)CH_2OH$ counter-ion (Claimed in WO 2005/028749 A1)

Example 1 is followed up to the point where the oil from the first phase separation (1990 parts) is diluted with water (1570 parts). The solution so-formed is then treated at 50° C. with a solution of 196 parts 2-amino-2-methyl-1-propanol in 350 parts cold water and 127 parts citric acid. The mixture is stirred at 50° C. for 10 minutes, then cooled to 20° C. After standing for 1 hour, the lower phase of oil is separated, and diluted with water to 5000 parts.

After standing for 1 hour, the lower phase of oil is separated, and diluted with water to give 4400 parts of an aqueous solution containing 22.0% of a compound of formula (6).

parts). After standing for 1 hour, the lower phase of oil is separated, and diluted with water to give 4400 parts of an aqueous solution containing 20.3% of a compound of formula (A, M=Na).

The aqueous solution so-formed precipitates on cooling to room temperature.

Application Example 1

The product from Preparative Example 1 is added at a range of concentrations from 0.2 to 2% by weight dry fibre to 200 parts of a 2.5% aqueous suspension of a 50:50 mixture of bleached spruce sulphite cellulose and bleached beech sulphite cellulose beaten to a Schopper Riegler wetness of 20° SR. The suspension is stirred for 5 minutes, then diluted to 1000 parts. A paper sheet is then made by drawing the suspension through a wire mesh. After being pressed and dried, the paper is measured for whiteness on a Minolta CM-700d spectrophotometer.

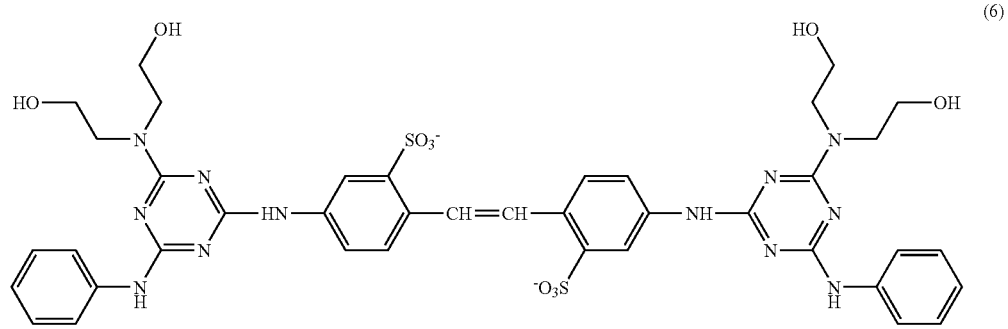

(6)

$[Na^+]_{0.7}[(CH_3)_2C(NH_3^+)CH_2OH]_{1.3}$

The aqueous solution so-formed precipitates within 4 days on storage at 4° C. in the presence of crystal seeds.

Example 8

Comparative Example to Show Advantage Over the $Na^+$ Counter-Ion

Example 1 is followed up to the point where the oil from the first phase separation (1990 parts) is diluted with water (1570

TABLE 1

| Conc. (%) | CIE Whiteness |
| --- | --- |
| 0 | 75.8 |
| 0.2 | 112.2 |
| 0.4 | 124.9 |
| 0.8 | 133.8 |
| 1.2 | 140.5 |

TABLE 1-continued

| Conc. (%) | CIE Whiteness |
|---|---|
| 1.6 | 142.6 |
| 2.0 | 143.5 |

The results in Table 1 clearly demonstrate the excellent whitening effect afforded by a compound of the invention.

Application Example 2

A coating composition is prepared containing 500 parts chalk (commercially available under the trade name Hydrocarb 90 from OMYA), 500 parts clay (commercially available under the trade name Kaolin SPS from IMERYS), 470 parts water, 6 parts dispersing agent (a sodium salt of a polyacrylic acid commercially available under the trade name Polysalz S from BASF), 200 parts latex (an acrylic ester copolymer commercially available under the trade name Acronal S320D from BASF), 40 parts of a 10% solution of polyvinyl alcohol (commercially available under the trade name Mowiol 4-98 from Kuraray) in water, and 50 parts of a 10% solution of carboxymethyl cellulose (commercially available under the trade name Finnfix 5.0 from Noviant) in water. The solids content is adjusted to 60% by the addition of water, and the pH is adjusted to 8-9 with sodium hydroxide.

The product from Preparative Example 1 is added at 0.5, 1.0 and 1.5% concentration to the stirred coating composition. The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. The dried paper is allowed to condition, then measured for CIE Whiteness on a calibrated Elrepho spectrophotometer.

TABLE 2

| Conc. (%) | CIE Whiteness |
|---|---|
| 0 | 90.2 |
| 0.5 | 105.2 |
| 1.0 | 108.9 |
| 1.5 | 109.6 |

The results in Table 2 clearly demonstrate the excellent whitening effect afforded by a compound of the invention.

The invention claimed is:

1. An aqueous solution consisting essentially of 15 to 35% by weight of a compound of formula (1)

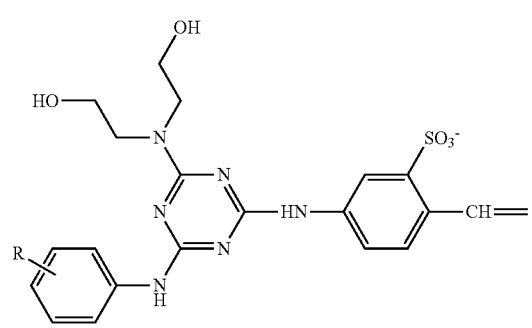

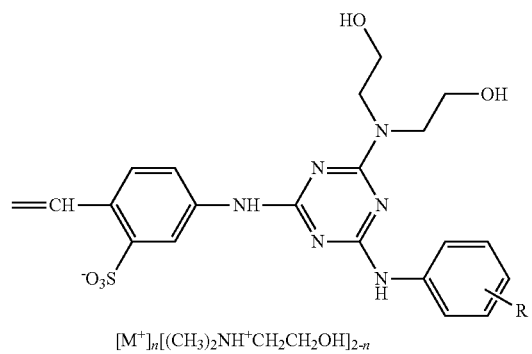

wherein

R is hydrogen or a methyl radical, $M^+$ is $Li^+$, $Na^+$, or $K^+$, n is less than or equal to 1.5, and of 0.1 to 2.0% by weight of an organic acid selected from the group consisting of citric acid, glycolic acid, acetic acid and formic acid.

2. An aqueous solution according to claim 1, consisting essentially of 15 to 35% by weight of a compound of formula (1) and wherein R is hydrogen or a methyl radical, $M^+$ is $Na^+$, and n is less than or equal to 1.5, and of 0.1 to 2% by weight of citric acid.

3. An aqueous solution according to claim 2, wherein

R is hydrogen, $M^+$ is $Na^+$, and n is less than or equal to 1.5.

4. An aqueous solution according to claim 2, wherein

R is hydrogen, $M^+$ is $Na^+$, and n is less than or equal to 1.2.

5. An aqueous solution according to claim 1, further comprising one or more carriers, antifreezes, defoamers, solubilizing aids, preservatives, complexing agents or organic by-products.

6. A process for preparing an aqueous solution, wherein the aqueous solution comprises 10 to 40% by weight of a compound of formula (1)

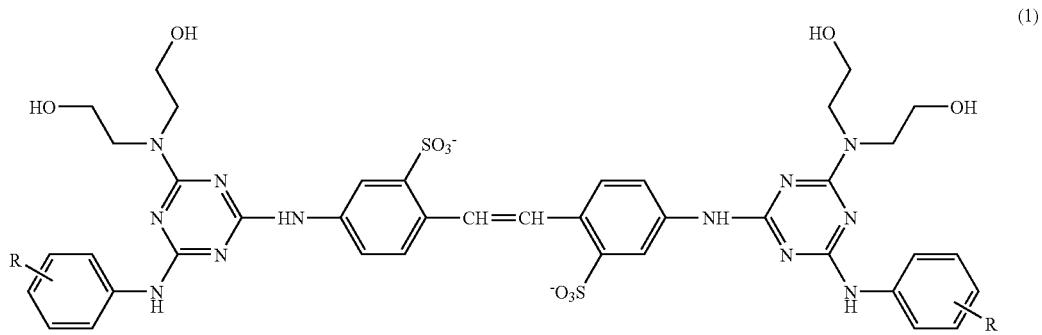

wherein
R is hydrogen or a methyl radical,
$M^+$ is $Li^+$, $Na^+$, or $K^+$,
n is less than or equal to 1.5, and of 0.05 to 5% by weight of an organic acid selected from the group consisting of citric acid, glycolic acid, acetic acid and formic acid, comprising the step of converting a compound of formula (2)

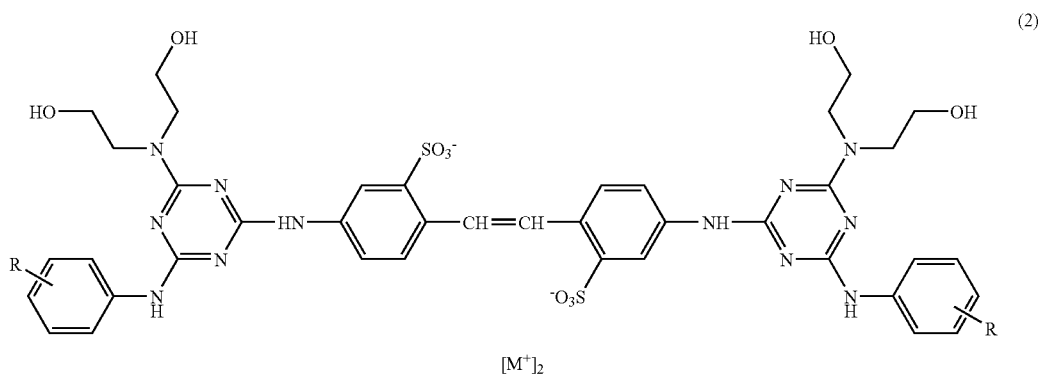

wherein
R is defined as above,
in the form of an aqueous solution to a mixed salt form (1) in which at least 25% of the $M^+$ ions associated with the sulphonate groups have been replaced by $(CH_3)_2NH^+CH_2CH_2OH$ ions, by treatment with 2-dimethylaminoethanol and an organic acid.

7. An optical brightener for textiles, paper, board and nonwovens comprising an aqueous solution as claimed in claim 1.

8. An aqueous suspension of pulp comprising an aqueous solution as claimed in claim 1.

9. A process for whitening of paper comprising the steps of
providing a pulp suspension,
adding 0.01 to 2% by weight based on dry fibre of an aqueous solution
wherein the aqueous solution consists essentially of 15 to 35% by weight of a compound of formula (1)

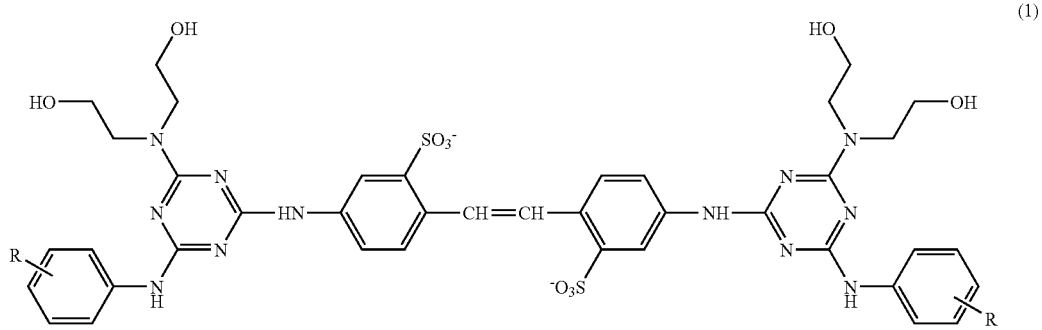

wherein
R is hydrogen or a methyl radical,
M is Li⁺, Na⁺, or K⁺,
n is less than or equal to 1.5, and
0.1 to 2% by weight of an organic acid selected from the group consisting of citric acid, glycolic acid, acetic acid and formic acid,
producing a paper sheet from the pulp suspension,
pressing and drying the paper sheet.

10. A process for whitening of paper comprising the steps of
preparing an aqueous coating composition by mixing together chalk or other white pigments, one or more dispersing agents, a primary latex binder and optionally a secondary binder, and optionally other additives,
adding 0.01 to 3% by weight based on dry pigment of an aqueous solution
wherein the aqueous solution consists essentially of 15 to 35% by weight of a compound of formula (1)

of 0.1 to 2% by weight of an organic acid selected from the group consisting of citric acid, glycolic acid, acetic acid and formic acid,
applying the coating composition to a paper sheet to form a coated paper sheet, and
drying the coated paper sheet.

11. An aqueous solution according to claim 1, which is free from solubilising auxiliaries.

12. An aqueous solution according to claim 1, which is stable to storage at 4° C. for at least two weeks either in the absence or presence of crystal seeds.

13. An aqueous solution according to claim 1, wherein the organic acid comprises citric acid.

14. An aqueous solution according to claim 1, wherein the organic acid comprises glycolic acid.

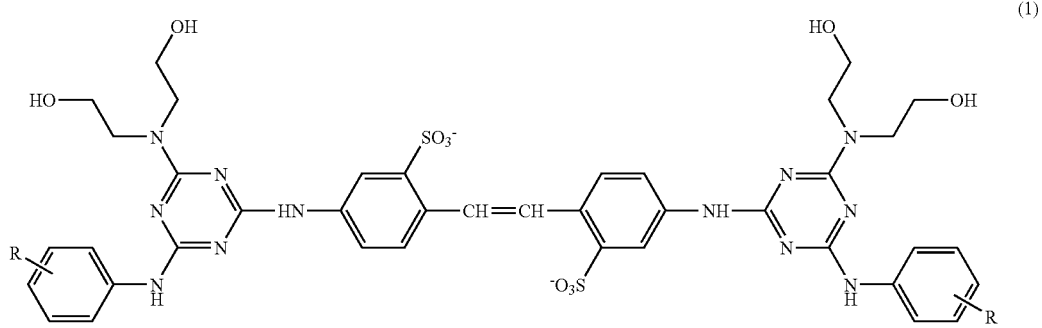

wherein
R is hydrogen or a methyl radical,
M⁺ is Li⁺, Na⁺, or K⁺,
n is less than or equal to 1.5, and 15. An aqueous solution according to claim 1, wherein the organic acid comprises acetic acid.

16. An aqueous solution according to claim 1, wherein the organic acid comprises formic acid.

* * * * *